(12) United States Patent
Tennican

(10) Patent No.: US 9,192,443 B2
(45) Date of Patent: Nov. 24, 2015

(54) COMBINED CAP APPLICATORS

(71) Applicant: Hyprotek, Inc., Spokane, WA (US)

(72) Inventor: Patrick O. Tennican, Spokane, WA (US)

(73) Assignee: Hyprotek, Inc., Spokane, WA (US)

( * ) Notice: Subject to any disclaimer, the term of this patent is extended or adjusted under 35 U.S.C. 154(b) by 288 days.

(21) Appl. No.: 13/757,465

(22) Filed: Feb. 1, 2013

(65) Prior Publication Data

US 2013/0199947 A1 Aug. 8, 2013

Related U.S. Application Data

(60) Provisional application No. 61/595,635, filed on Feb. 6, 2012.

(51) Int. Cl.
| | |
|---|---|
| *B43K 5/00* | (2006.01) |
| *A61B 19/02* | (2006.01) |
| *B65B 5/00* | (2006.01) |
| *B05C 1/00* | (2006.01) |
| *A61F 13/40* | (2006.01) |
| *B65D 75/40* | (2006.01) |
| *A61F 13/02* | (2006.01) |
| *A61F 15/00* | (2006.01) |
| *A61M 5/158* | (2006.01) |
| *A61F 13/00* | (2006.01) |

(52) U.S. Cl.
CPC .......... *A61B 19/0256* (2013.01); *A61F 13/0253* (2013.01); *A61F 15/004* (2013.01); *A61M 5/158* (2013.01); *A61M 35/006* (2013.01); *B05C 1/00* (2013.01); *B65B 5/00* (2013.01); *B65D 75/40* (2013.01); *A61F 13/00063* (2013.01); *A61F 15/005* (2013.01); *A61M 2005/1586* (2013.01)

(58) Field of Classification Search
CPC ........ A61M 35/006; B05C 1/00; B65D 75/40
USPC .......................................... 401/132–133, 202
See application file for complete search history.

(56) References Cited

U.S. PATENT DOCUMENTS

| 3,860,348 | A | * | 1/1975 | Doyle ............................. 401/6 |
| 4,291,697 | A | | 9/1981 | Georgevich |
| 4,440,207 | A | * | 4/1984 | Genatempo et al. .......... 150/154 |

(Continued)

FOREIGN PATENT DOCUMENTS

| CN | 2546003 | 4/2003 |
| CN | 2705167 | 6/2005 |

(Continued)

OTHER PUBLICATIONS

PCT Search Report mailed May 15, 2013 for PCT application No. PCT/US13/24635, 10 pages.

(Continued)

*Primary Examiner* — Jennifer C Chiang
(74) *Attorney, Agent, or Firm* — Lee & Hayes, PLLC

(57) ABSTRACT

A combined cap applicator may be used in combination with one or more cleansing, antimicrobial and/or antiseptic agents to reduce or eliminate contaminates on a surface. According to some embodiments, the combined cap applicators may comprise a first and second cap where each cap contains an applicator. According to some embodiments, the applicator may be coated or infused with a cleansing, antimicrobial or antiseptic agents for use on a surface.

19 Claims, 6 Drawing Sheets

(56) References Cited

U.S. PATENT DOCUMENTS

| | | | |
|---|---|---|---|
| 4,830,856 A | 5/1989 | Peppers | |
| 4,893,956 A * | 1/1990 | Wojcik et al. | 401/130 |
| 5,015,228 A | 5/1991 | Columbus et al. | |
| 5,046,608 A | 9/1991 | Laipply | |
| 5,438,984 A | 8/1995 | Schoendorfer | |
| 5,554,135 A | 9/1996 | Menyhay | |
| 5,556,375 A | 9/1996 | Ewall | |
| 5,637,080 A | 6/1997 | Geng | |
| 5,713,842 A | 2/1998 | Kay | |
| 5,730,530 A | 3/1998 | Stoddard et al. | |
| 5,732,716 A | 3/1998 | Utecht | |
| 5,779,053 A | 7/1998 | Partika et al. | |
| 5,846,559 A | 12/1998 | Hopp | |
| 5,973,221 A | 10/1999 | Collyer et al. | |
| 6,063,029 A | 5/2000 | Saita et al. | |
| 6,168,800 B1 | 1/2001 | Dobos et al. | |
| 6,455,066 B1 | 9/2002 | Fischer et al. | |
| 7,282,186 B2 | 10/2007 | Lake, Jr. et al. | |
| 7,478,962 B2 * | 1/2009 | De Laforcade | 401/262 |
| 7,482,021 B1 | 1/2009 | Tison et al. | |
| 7,780,794 B2 * | 8/2010 | Rogers et al. | 134/6 |
| 7,799,010 B2 | 9/2010 | Tennican | |
| 8,065,773 B2 * | 11/2011 | Vaillancourt et al. | 15/104.94 |
| 8,273,303 B2 * | 9/2012 | Ferlic et al. | 422/294 |
| 8,336,152 B2 * | 12/2012 | Vaillancourt et al. | 15/104.94 |
| 8,496,625 B2 | 7/2013 | Brugger et al. | |
| 8,647,326 B2 | 2/2014 | Solomon et al. | |
| 8,777,504 B2 * | 7/2014 | Shaw et al. | 401/202 |
| 8,778,387 B2 * | 7/2014 | Tennican et al. | 424/447 |
| 2003/0007939 A1 | 1/2003 | Murad | |
| 2004/0037789 A1 | 2/2004 | Moneuze et al. | |
| 2004/0110841 A1 | 6/2004 | Kite et al. | |
| 2005/0034731 A1 | 2/2005 | Rousseau et al. | |
| 2005/0084521 A1 | 4/2005 | Hamada et al. | |
| 2005/0129897 A1 | 6/2005 | Zhou et al. | |
| 2005/0265773 A1 | 12/2005 | De Laforcade | |
| 2006/0129117 A1 | 6/2006 | Malowaniec | |
| 2006/0142684 A1 | 6/2006 | Shanbrom | |
| 2006/0151347 A1 | 7/2006 | Grossman | |
| 2007/0179373 A1 | 8/2007 | Pronovost | |
| 2007/0255193 A1 | 11/2007 | Patel et al. | |
| 2008/0057136 A1 | 3/2008 | Polyakov et al. | |
| 2008/0119801 A1 | 5/2008 | Moore | |
| 2008/0181950 A1 | 7/2008 | Bates et al. | |
| 2009/0010998 A1 | 1/2009 | Marchitto et al. | |
| 2009/0012496 A1 | 1/2009 | Tennican | |
| 2009/0028750 A1 * | 1/2009 | Ryan | 422/28 |
| 2009/0036541 A1 | 2/2009 | Mardis | |
| 2009/0324508 A1 | 12/2009 | Bobbert | |
| 2010/0030170 A1 | 2/2010 | Keller et al. | |
| 2010/0050351 A1 * | 3/2010 | Colantonio et al. | 15/104.93 |
| 2010/0078336 A1 | 4/2010 | Reyhan et al. | |
| 2010/0163435 A1 | 7/2010 | Fischer et al. | |
| 2010/0260865 A1 * | 10/2010 | Kritzler | 424/616 |
| 2011/0052664 A1 | 3/2011 | Tennican et al. | |
| 2011/0184382 A1 | 7/2011 | Cady | |
| 2011/0265834 A1 | 11/2011 | Tennican | |
| 2012/0288571 A1 | 11/2012 | Tennican et al. | |
| 2013/0138085 A1 * | 5/2013 | Tennican | 604/533 |
| 2013/0287860 A1 | 10/2013 | Tennican et al. | |
| 2014/0243725 A1 | 8/2014 | Tennican et al. | |

FOREIGN PATENT DOCUMENTS

| | | |
|---|---|---|
| CN | 1711845 | 12/2005 |
| CN | 1813097 | 8/2006 |
| EP | 0262792 | 4/1988 |
| EP | 1687039 | 1/2009 |
| GB | 350384 | 6/1931 |
| JP | 07500751 | 1/1995 |
| JP | 10110268 | 4/1998 |
| JP | 2001525688 | 12/2001 |
| JP | 2004049540 | 2/2004 |
| JP | 2005511147 | 4/2005 |
| JP | 2005350571 A * | 12/2005 |
| JP | 2006503647 | 2/2006 |
| JP | 2006526664 | 11/2006 |
| JP | 2007505093 | 3/2007 |
| JP | 2007536261 | 12/2007 |
| JP | 2008503485 | 2/2008 |
| JP | 2009519312 | 5/2009 |
| JP | 2013503713 | 2/2013 |
| WO | WO8503275 | 8/1985 |
| WO | WO9204923 | 4/1992 |
| WO | WO9308777 | 5/1993 |
| WO | WO0156540 | 8/2001 |
| WO | WO2004091675 | 10/2004 |
| WO | WO2004108091 | 12/2004 |
| WO | WO2005003436 | 1/2005 |
| WO | WO2005025486 | 3/2005 |
| WO | WO2005062896 | 7/2005 |
| WO | WO2005089341 | 9/2005 |
| WO | WO2006009853 | 1/2006 |
| WO | WO2006/089139 A2 | 8/2006 |
| WO | WO2007068938 | 6/2007 |
| WO | WO2007137056 | 11/2007 |
| WO | WO2008003779 | 1/2008 |
| WO | WO2008009925 | 1/2008 |
| WO | WO2009076718 | 6/2009 |
| WO | WO2011019132 | 7/2011 |
| WO | WO2011163124 | 12/2011 |
| WO | WO2013082187 | 6/2013 |

OTHER PUBLICATIONS

The PCT Search Report mailed May 13, 2013 for PCT application No. PCT/US13/24644, 10 pages.

Tjhe PCT Search Report mailed May 15, 2013 for PCT application No. PCT/US13/24651, 12 pages.

The PCT Search report mailed May 31, 2013 for PCT application No. PCT/US13/24649, 14 pages.

Office action for U.S. Appl. No. 13/757,318, mailed on Aug. 26, 2014, Tennican, "Antiseptic Applicators and Packaging Techniques", 9 pages.

Office action for U.S. Appl. No. 13/757,423, mailed on Sep. 4, 2014, Tennican, "Adhesive Patch with Antimicrobial Composition", 13 pages.

The Australian Office Action mailed Nov. 4, 2013 for Australian patent application No. 2010289415, a counterpart foreign application of U.S. Appl. No. 12/874,188, 3 pages.

The Australian Office Action mailed Mar. 13, 2014 for Australian patent application No. 2011207398, a counterpart foreign application of U.S. Appl. No. 13/554,962, 3 pages.

Translated Chinese Office Action mailed Oct. 17, 2013 for Chinese patent application No. 201180006632.3, a counterpart foreign application of U.S. Appl. No. 13/554,962, 13 page.

Translated Chinese Office Action mailed Oct. 23, 2014 for Chinese patent application No. 201080047665.8, a counterpart foreign application of U.S. Pat. No. 8,778,387, 13 pages.

Translated Chinese Office Action mailed Apr. 10, 2014 for Chinese patent application No. 201180006632.3, a counterpart foreign application of U.S. Appl. No. 13/554,962, 19 pages.

Translated Chinese Office Action mailed Apr. 22, 2014 for Chinese patent application No. 201080047665.8, a counterpart foreign application of U.S. Appl. No. 12/874,188, 17 pages.

Translated Chinese Office Action mailed Aug. 12, 2013 for Chinese patent application No. 201080047665.8, a counterpart foreign application of U.S. Appl. No. 12/874,188, 13 pages.

Translated Chinese Office Action mailed Sep. 25, 2014 for Chinese patent application No. 201180006632.3, a counterpart foreign application of U.S. Appl. No. 13/554,962, 19 pages.

The European Office Action mailed Sep. 12, 2014 for European patent application No. 11701925.7, a counterpart foreign application of U.S. Pat. No. 8,846,008, 5 pages.

The European Search Report mailed Apr. 23, 2014 for European patent application No. , 11 pages.

Final Office Action for U.S. Appl. No. 13/554,962, mailed on Dec. 5, 2013, Patrick O. Tennican, "Antimicrobial Agents and Methods of Use", 14 pages.

(56) References Cited

OTHER PUBLICATIONS

Hospenthal et al., "Guidelines for the Prevention of Infections After Combat-Related Injuries", Journal of TRAUMA Injury, Infection, and Critical Care, vol. 64, No. 3, Mar. 2008, pp. S211-S220.
Translated Japanese Office Action mailed Aug. 19, 2014 for Japanese patent application No. 2012-528071, a counterpart foreign application of U.S. Pat. No. 8,778,387, 10 pages.
Japanese Patent No. JP6501857, which corresponds to International Patent Publication No. WO92/04923.
McGee et al., "Preventing Complications of Central Venous Catheterization", The New England Journal of Medicine, vol. 348, No. 12, Mar. 20, 2003, pp. 1123-1133.
The Mexican Office Action mailed Jul. 2, 2014 for Mexican patent application No. MX/a/2012/008482, a counterpart foreign application of U.S. Appl. No. 13/554,962, 2 pages.
The Mexican Office Action mailed May 26, 2014 for Mexican patent application No. MX/a/2012/002746, a counterpart foreign application of U.S. Pat. No. 8,778,387, 4 pages.
Office Action for U.S. Appl. No. 13/924,410, mailed on Nov. 22, 2013, Patrick O. Tennican, "Antimicrobial Agents and Methods of Use", 15 pages.
Final Office Action for U.S. Appl. No. 12/874,188, mailed Dec. 19, 2012, Patrick O. Tennican et al., "Antimicrobial Medical Dressings and Protecting Wounds and Catheter Sites", 6 pages.
Non-Final Office Action for US Patent Application mailed on Feb. 15, 2013, Patrick O. Tennican et al., "Antimicrobial Agents and Methods of Use", 12 pages.
Non-Final Office Action for U.S. Appl. No. 12/874,188, mailed Feb. 7, 2014, Patrick O. Tennican et al., "Antimicrobial Medical Dressings and Protecting Wounds and Catheter Sites", 6 pages.
Office Action for U.S. Appl. No. 13/924,410, mailed on Mar. 28, 2014, Patrick O. Tennican, "Antimicrobial Agents and Methods of Use", 18 pages.
Non-Final Office Action for U.S. Appl. No. 12/874,188, mailed Jun. 29, 2012, Patrick O. Tennican et al., "Antimicrobial Medical Dressings and Protecting Wounds and Catheter Sites", 6 pages.
Office action for U.S. Appl. No. 12/874,188, mailed on Sep. 10, 2013, Tennican et al., "Antimicrobial Medical Dressings and Protecting Wounds and Catheter Sites", 6 pages.
Office action for U.S. Appl. No. 14/271,365, mailed on Sep. 11, 2014, Tennican et al., "Antimicrobial Medical Dressings and Protecting Wounds and Catheter Sites", 7 pages.
The PCT Search Report mailed May 20, 2011 for PCT Appliction No. PCT/US10/47756.
The PCT Search Report mailed Aug. 1, 2011 for PCT application No. PCT/US11/22150.
Singhal et al., "Wound Infection", eMedicine from WebMD <<http://www.emedicine,medscape.com>>, Updated Sep. 15, 2009, 32 pages.
"VERSENE Acid—Solubility", The Dow Chemical Company, Sep. 15, 2010, pp. 1-3.
"VERSENE NA Disodium EDTA Chelating Agent", The Dow Chemical Company, Oct. 2009, pp. 1-2.
The Translated Chinese Office Action mailed Apr. 8, 2015 for Chinese patent application No. 201180006632.3, a counterpart foreign application of U.S. Pat. No. 8,846,008, 19 pAGES.
The Translated Chinese Office Action mailed Apr. 9, 2015 for Chinese patent application No. 201080047665.8, a counterpart foreign application of U.S. Pat. No. 8,778,387, 8 pages.
The Translated Japanese Office Action mailed Dec. 24, 2014 for Japanese patent application No. 2012-550177, a counterpart foreign application of U.S. Pat. No. 8,846,008, 4 pages.
The Translated Japanese Office Action mailed Apr. 14, 2015 for Japanese patent application No. 2012-528071, a counterpart foreign application of U.S. Pat. No. 8,778,387, 9 pages.
The Mexican Office Action mailed Jan. 13, 2015 for Mexican patent application No. MX/a/2012/002746, a counterpart foreign application of U.S. Pat. No. 8,778,387, 2 pages.
Office Action for U.S. Appl. No. 14/271,365, mailed on Jan. 23, 2015, Patrick O. Tennican, "Antimicrobial Medical Dressings and Protecting Wounds and Catheter Sites", 8 pages.
Office Action for U.S. Appl. No. 13/934,135, mailed on Mar. 12, 2015, Patrick O. Tennican, "Antimicrobial Agents and Methods of Use", 14 pages.
Non-Final Office Action for U.S. Appl. No. 13/757,423, mailed on Apr. 10, 2015, Patrick O. Tennican, "Adhesive Patch with Antimicrobial Composition", 13 pages.
Translated Russian Office Action mailed Jan. 23, 2015 for Russian patent applcation No. 2012136147, a counterpart foreign application of US patent application No. , pages.
The Extended European Search Report mailed Mo Sep. 10, 2015 for European Patent Application No. 13747071.2, 8 pages.
The Extended European Search Report mailed Sep. 11, 2015 for European Patent Application 13746209.9, 6 pages.
The Extended European Search Report mailed Sep. 17, 2015 for European patent application No. 13746984.7, 7 pages.
The Extended European Search Report mailed Sep. 18, 2015 for European Patent Application No. 13746515.9, 7 pages.
The Translated Japanese Office Action mailed Aug. 11, 2015 for Japanese patent application No. 2012-550177, a counterpart foreign application of U.S. Pat. No. 8,846,008, 4 pages.

* cited by examiner

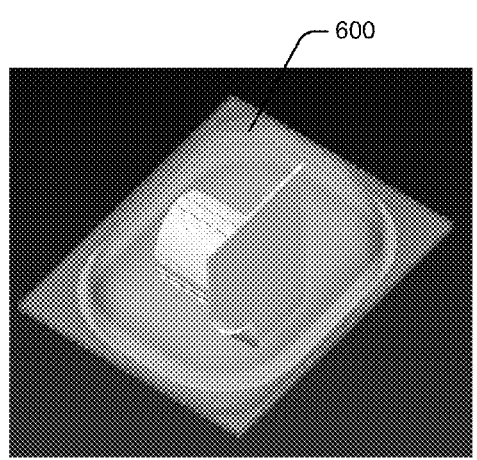
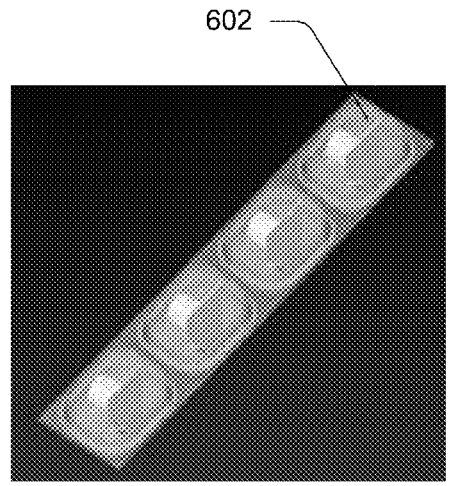
FIG. 6A    FIG. 6B
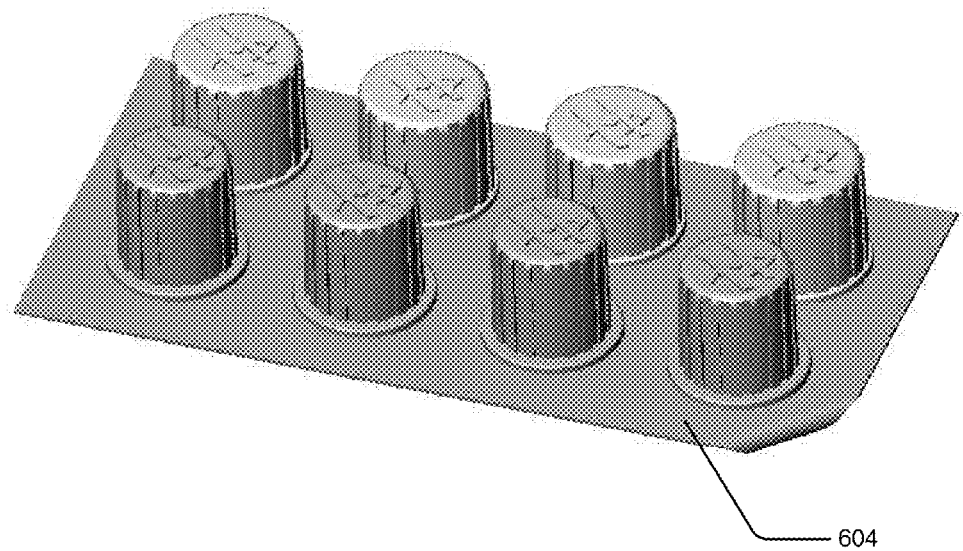
FIG. 6C

COMBINED CAP APPLICATORS

CROSS REFERENCE TO RELATED APPLICATION

This claims priority to U.S. Provisional Patent Application No. 61/595,635 filed on Feb. 6, 2012 entitled "Antiseptic Applicators and Protective Devices," which is hereby incorporated by reference in its entirety.

BACKGROUND

Healthcare acquired infection (HAI) has been recognized as a significant cause of preventable mortality and morbidity. In the United States, HAI annually costs nearly 99,000 lives and billions of dollars in additional treatment and hospitalization. Klevens, et al., *Estimating Health Care-Associated Infection and Deaths in U.S. Hospitals,* 2002, Public Health Reports, Vol. 122, p. 160, 2007. Contamination of intravascular catheters, surgical sites and invasive procedure sites, frequently leads to device removal and replacement, prolonged parenteral antimicrobial therapy, and extended hospitalizations and rehabilitation.

The spread of multi-antimicrobial resistant organisms frequently are spread by healthcare providers' hands or medical equipment, from one colonized or infected patient to other susceptible patients. Surgical site infections may result from inadequate antiseptic preparations of the skin. Widespread use of chlorhexidine gluconate (CHG) for routine washing and wiping of pre-operative sites, has led to the increased incidence of resistant *Staphyloccus aureus*, both to methicillin (MRSA) and CHG, in some hospital environments.

BRIEF DESCRIPTION OF THE DRAWINGS

The detailed description is set forth with reference to the accompanying figures. In the figures, the left-most digit(s) of a reference number identifies the figure in which the reference number first appears. The use of the same reference numbers in different figures indicates similar or identical items or features.

FIGS. 6A-6C illustrate various ways of packaging an example protective device.

DETAILED DESCRIPTION

Overview

Figure 1A:
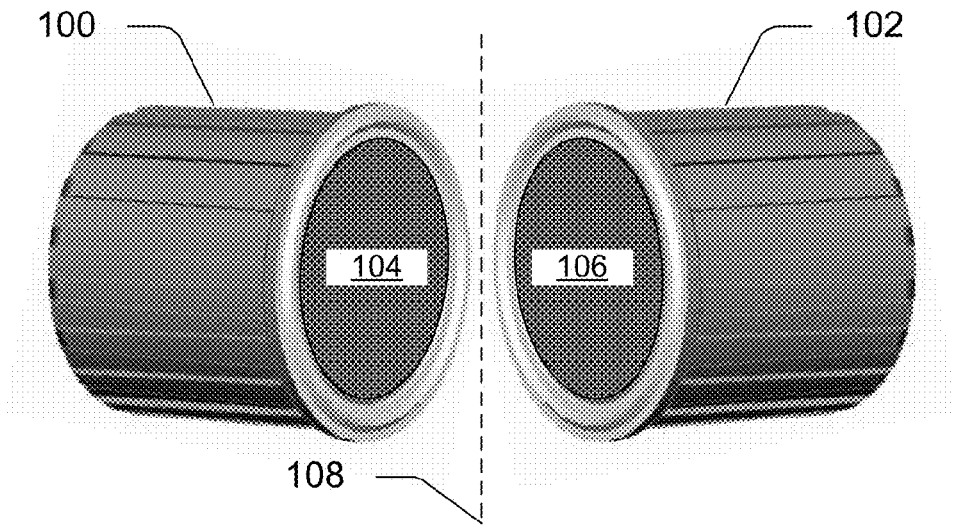
FIGS. 1A and 1B illustrate an example combine cap applicator.

This disclosure describes medical combined cap applicators and protective cap devices designed to reduce and/or prevent infections. In one embodiment, the disclosure describes example combined cap applicators. The combined cap applicators may comprise a first cap and a second cap detachably coupled together. The caps are separable to expose a receptacle or interior cavity within each cap. Each receptacle within each cap containing a permeable foam applicator material that may be coated or filled with, for example, a cleansing, antiseptic or antimicrobial composition.

In another embodiment, the disclosure describes example protective cap devices for multiple dose/use vials. The protective cap device may contain a foam material impregnated with an antimicrobial composition that, upon application of the protective cap device to a multiple dose/use vial, bathes the metal ring and elastomeric stopper of the vial in the antimicrobial composition. Thereby, reducing and/or preventing the presence of one or more contaminants upon a multiple dose/use vial. Furthermore, the foam material is constructed so as to prevent contamination of the contents of a multiple use/dose vial.

The detailed discussion below begins with a section entitled "Example Antimicrobial Composition", which describes in detail an example antimicrobial composition that may be included in the medical applicators and devices described herein. Next, the disclosure describes the "Example Combined Cap Applicators." Next, the disclosure describes "Example Process" for using an example combine cap applicator. The next sections entitled "Example Protective Cap Device" and "Example Packaging of Protective Cap Device" describes in detail several example capping devices for use on multiple dose/use vials. Next, the disclosure describes "Other Cap Devices." Finally, the disclosure concludes with a brief "Conclusion."

This overview, including section titles, is provided to introduce a selection of concepts in a simplified form that are further described below. The overview is provided for the reader's convenience and is not intended to limit the scope of the claims, nor the proceeding sections.

Example Antimicrobial Composition

In one example embodiment, antimicrobial compositions that may be used in connection with the approaches described herein may include those described in, for example, U.S. Provisional Patent Application No. 61/412,375, filed Nov. 10, 2010 to Tennican et al., which is incorporated herein by reference. For example, the antimicrobial compositions may include water ($H_2O$), a strong and non-toxic chelating agent such as ethylenediaminetetraacetic acid (EDTA)(e.g., disodium EDTA, calcium disodium EDTA, magnesium EDTA, potassium EDTA, gallium EDTA,) or sodium citrate (or acids, salts, derivatives, or other forms of EDTA or sodium citrate), a short-chain monohydric alcohol (e.g., ethanol with a molecular formula of $C_2H_5OH$ and an empirical formula of $C_2H_6O$), and a strong, small molecule oxidizing agent such as hydrogen peroxide ($H_2O_2$). In one specific example, the compositions may consist essentially of water, EDTA, ethanol, and hydrogen peroxide. Additional ingredients can include thickeners, gellants, surfactants, foamers and/or foam stabilizers. However, in other examples, other antimicrobial compositions may be used in combination with the applicators and devices described in this disclosure.

In one embodiment, the present application provides an antimicrobial composition comprising (a) water; (b) a low molecular weight alcohol; (c) a peroxide or peroxide-generating agent; and (d) a chelating agent.

In some embodiments, the alcohol in the antimicrobial composition comprises ethanol. In some embodiments, the alcohol is present in the antimicrobial composition at a concentration of from about 1% to about 95% by volume. In other embodiments, the alcohol is present from about 20% to about 70% by volume. In alternative embodiments, the alcohol is present at about 50% by volume.

In some embodiments, the chelating agent in the antimicrobial composition comprises ethylenediamine tetraacetic acid (EDTA). In some embodiments, the EDTA is present at a concentration of from about 5 mg/mL to about 50 mg/mL. In other embodiments, the EDTA is present at a concentration of about 10 mg/mL.

In some embodiments, the peroxide or peroxide-generating agent in the antimicrobial composition comprises hydrogen peroxide ($H_2O_2$). In some embodiments, the $H_2O_2$ is present at a concentration of from about 0.05% to about 40% by volume. In other embodiments, the $H_2O_2$ is present at a concentration of from about 0.5% to about 7.5% by volume. In alternative embodiments, the $H_2O_2$ is present at a concentration of about 1.5% by volume.

The antimicrobial compositions may be in a liquid form or a gel form, and may be combined with one or more carriers or diluents, depending on the needs of a specific application. For example, if the antimicrobial composition is used as a cleaning agent the antimicrobial composition may be in a liquid form. In that case, the concentration of the various constituents may depend on, for example, a desired level of sanitation and/or disinfection, whether the composition is being applied directly to living tissue or to a medical device, and/or to avoid irritation of tissue to which the composition will be applied directly or indirectly (e.g., via a medical device to which the composition is or was applied).

In addition to providing disinfection at the time of the application, the antimicrobial compositions may also provide a lasting barrier against contamination. For example, even after volatile constituents of the composition (e.g., water, alcohol, hydrogen peroxide, etc.) have evaporated, the chelating agent may remain on the treated surfaces (e.g., multiple use vial or port cleaning/protecting device, stethoscope, fingers, surrounding tissue, etc.) as a barrier that will provide antibacterial, antifungal or sporicidal (e.g., preventing germination of the spores), anti-parasitic, spermicidal or spermiostatic (e.g., decrease the motility of spermatozoon) and anti-viral qualities. By robbing the environment of components (e.g., iron, magnesium, and manganese) that are needed for the bacteria, spores, parasites, fungus and viruses to reproduce, the chelating agent provides a lasting defense to contamination even after other constituents of the antimicrobial composition have evaporated. Furthermore, the hydrogen peroxide in the antimicrobial compositions may induce a charge on a surface of materials (e.g., silicone materials) to which the antimicrobial compositions are applied, which make the materials more resistant to bacteria or other microorganisms.

In some embodiments, the antimicrobial composition described above may also provide a visual indication of contamination when applied to a surface or material, such indication may allow users to identify and clean surfaces to prevent infection.

If a surface or material is contaminated with bacteria, spores, parasites, viruses, bodily fluids, or other contaminants, the antimicrobial composition will begin to bubble or foam, providing a visual indicator of the contamination. The bubbling or foaming action is caused by reaction of the hydrogen peroxide with the bacteria, spores, parasites, and viruses. Specifically, contaminant enzymes that cause the hydrogen peroxide in the antimicrobial compositions to foam include, for example, catalases, superoxide dismutases (SOD), glutathione peroxidases, peroxiredoxin, and other peroxidases. Ooropharyngeal, respiratory, cervicovaginal secretions and serum would also contain hydrogen peroxide reactants or enzymes that would cause the antimicrobial compositions to foam. EDTA may attenuate these reactions somewhat. However, testing shows that the attenuation is mild and does not impair the ability of the antimicrobial compositions to visually indicate the presence of contamination. For example, *staphylococcus aureus* (MRSA) with catalase and *Pseudomonas aeruginosa* with SOD both produce vigorous bubbling on contact with antimicrobial compositions according to this application. The hydrogen peroxide will also produce bubbles or foam in response to a Fenton reaction with iron in the hemoglobin in red blood cells, or peroxidases in white blood cells and in the bodily fluids. The size and rate of bubble formation may be indicative of the level of contamination, giving the medical personnel a visual indication that the equipment is contaminated and a relative degree to which the equipment is contaminated (e.g., more or larger bubbles/foam indicates more contamination). Based on this indication medical personnel may determine that the equipment needs further cleaning and/or replacement to avoid infection.

The term "about" or "approximate" as used in context of describing the example antimicrobial composition is to be construed to include a reasonable margin of error that would be acceptable and/or known in the art.

Example Combined Cap Applicators

Figure 1B:
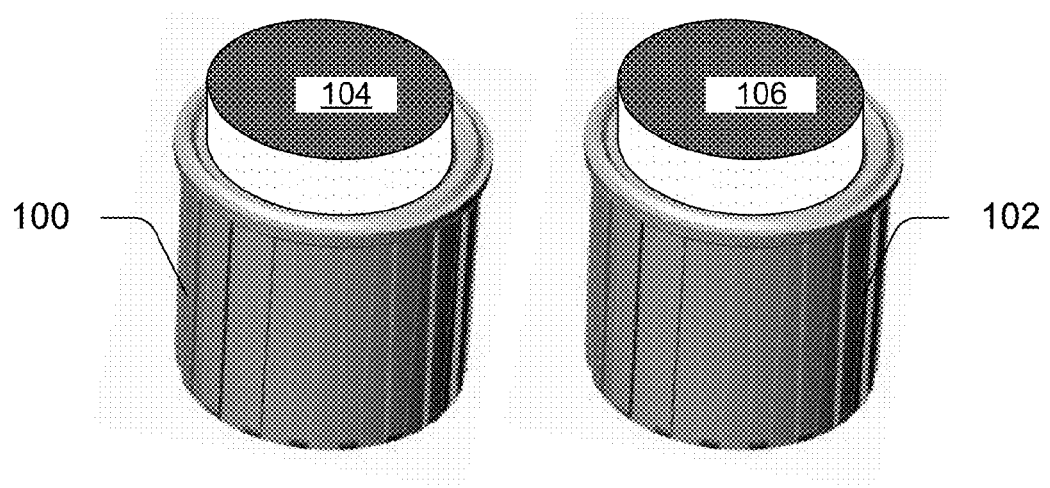

FIGS. 1A and 1B illustrate an example embodiment of a combine cap applicator in which a first cap applicator 100 may be detachably coupled to second cap applicator 102. Example materials for the composition of the first cap 100 and the second cap 102 include, but are not limited to, polypropylene, polyethylene and/or other copolymer materials. The first cap 100 and the second cap 102 may also comprise a material or agent that is UV protective to preserve the integrity of the antimicrobial composition during storage, shipping, etc. In other embodiments, the first cap 100 and the second cap 102 may comprise caps such as those described in U.S. patent application Ser. No. 13/688,044, filed Nov. 28, 2012 to Tennican et al., entitled "Port and Surface Cleaning Devices and Techniques," which is incorporated herein by reference.

FIGS. 1A and 1B illustrate one example embodiment in which both the first cap 100 and second cap 102 include an applicator material 104 and 106, respectively, disposed within a receptacle or interior cavity of each cap prior to use. When the first cap 100 and second cap 102 are coupled together along figurative line 108, the applicator material 104 and 106 of each protective cap may be in a state of compression. When the first and second caps 100 and 102 are detached from one another, the applicator material 104 and 106 may expand and/or protrude from the interior cavity of each cap for use in cleaning or disinfecting a desired site as illustrated by caps 100 and 102 in FIG. 1B (e.g., for disinfecting a intravascular port line, site preparation for a medical procedure or the like).

In some embodiments, the applicator material 104 and 106 housed within each cap is a permeable foam or sponge material, that may be coated or impregnated with a cleansing, antimicrobial, or antiseptic composition such as those described in the preceding section. Example materials for the composition of the applicator material 104 and 106 may include, but are not limited to starch polymer, cellulosic gel, polyurethane, silicone, silicone rubber, polyethylene, polypropylene, thermoplastic elastomer or mixtures thereof.

In some embodiments, the applicator material 104 and 106 may include, but are not limited to, different surface treatments (e.g., siping, slitting, etc.), surface finishes (e.g., macro-, micro-, or nano-structures, etc.), and/or contours (e.g., rounded, ribbed, protrusions, fingers, etc.) to provide cleaning and/or scrubbing effectiveness. In some embodiments, the applicator material in the first cap may be configured similar to the applicator material in the second cap (e.g., with the same surface treatments, finishes and/or contours).

However, in other embodiments, the applicator material in the first cap may be configured with a different surface treatments, finishes and/or contours than the applicator material in the second cap.

Further, while caps 100 and 102 and applicator material 104 and 106 are illustrated as being a generally cylindrical body, in other embodiments, the applicator material may take on other shapes and/or sizes. In some embodiments, the applicator material may have a shape that is substantially similar to the shape of the receptacle of the corresponding cap. For example, where the receptacle is cylindrical, the applicator material may also be cylindrical.

In some embodiments, the first cap 100 and the second cap 102 may be coupled together (e.g., during manufacture, packaging, assembly, etc.) by threads, a snap fit flange, a snap fit channel, a molded feature (e.g., the first cap may be custom cast in one of various shapes to uniquely correspond to the shape of the second cap thereby allowing a resin or adhesive, for example, to form a releasable seal when the first and second cap are attached), or the like. In some embodiments, the connection of the first cap 100 to the second cap 102 forms a seal to enclose the cleansing, antimicrobial, or antiseptic composition therein, thus preventing leakage or evaporation.

The first cap 100 may be removed or detached from the second cap 102 by, for example, twisting, pulling, snapping, or bending the first cap away from the second cap.

In other embodiments, each cap may be additionally sealed by a removable protective film or cover over the interior cavity that maintains the applicator material and cleansing, antimicrobial, or antiseptic composition in the respective caps. In some embodiments, each applicator material of each protective cap may contain a different cleansing, antimicrobial or antiseptic composition and/or different concentration of such composition.

In some embodiments, the first cap 100 may comprise a cap having an applicator material that protrudes from the receptacle of the cap, while the second cap 102 comprises a cap having applicator material that fits completely within and/or is recessed in a receptacle in the cap when in use. In that case, the first cap 100 with the protruding applicator material may be used to clean a surface (e.g., an intravascular line, valve, or port, an injection site, or the like) and the second cap 102 with the recessed applicator material may be used to cover and protect a port, vial, or other component (e.g., an intravascular line port, a vial, or the like).

In some embodiments, where the first or second cap may be configured to cover and/or protect a surface as described above, each of the first and second caps may have one of various example mechanisms for attaching each cap to the surface as described below in FIGS. 4C and 5A-5C.

Example Process

Figure 2:
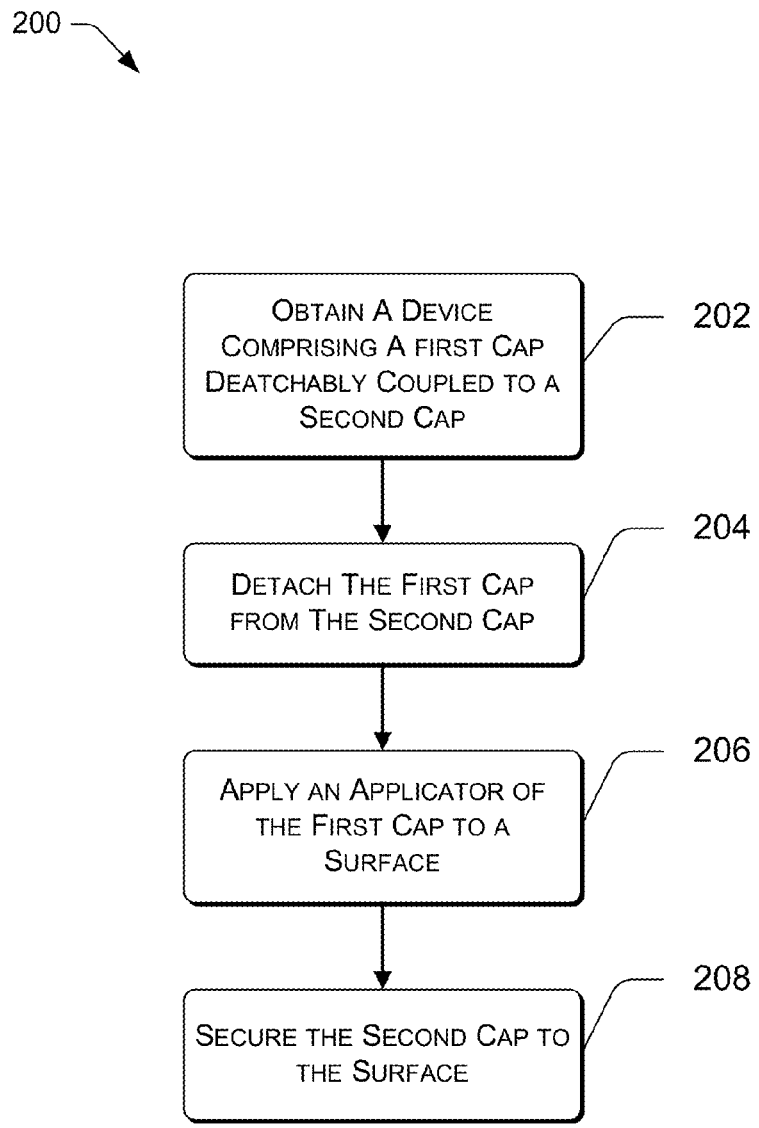
FIG. 2 is a flow diagram showing an example process for using an example combine cap applicator.

FIG. 2 illustrates an example process 200 for execution of the techniques described above of operating a combine cap applicator. The process 200 is illustrated as a logical flow graph. The order in which the operations are described is not intended to be construed as a limitation, and any number of the described operations can be combined in any order and/or in parallel to implement the process.

At operation 202, a device comprising a first cap detachably coupled to a second cap may be obtained. For example, such device may be any of the embodiments of the combined cap applicator as described above.

At operation 204, the first cap of the device may be detached from the second cap. In the context of FIG. 1, a user may detach the first cap by twisting, pulling, snapping or bending the first cap 100 away from the second cap 102.

At operation 206, an applicator located in the cavity of the first cap may be applied to a surface. Again, in the context of FIG. 1, the applicator 104 may be configured to extend beyond the cavity of the first cap when detached from the second cap. The applicator may be configured various surface treatments and/or contours for scrubbing, cleaning or disinfecting a surface (e.g., an intravascular line, valve, or port, an injection site, or the like).

Finally, at operation 208, the second cap may be removably secured to the surface. By securing the second cap to the surface, the surface may be protected from becoming re-contaminated by other environmental contaminants.

Example Protective Cap Device

Various example protective cap devices are described herein. Example protective cap devices are described generally with reference to FIG. 3-6.

Figure 3:
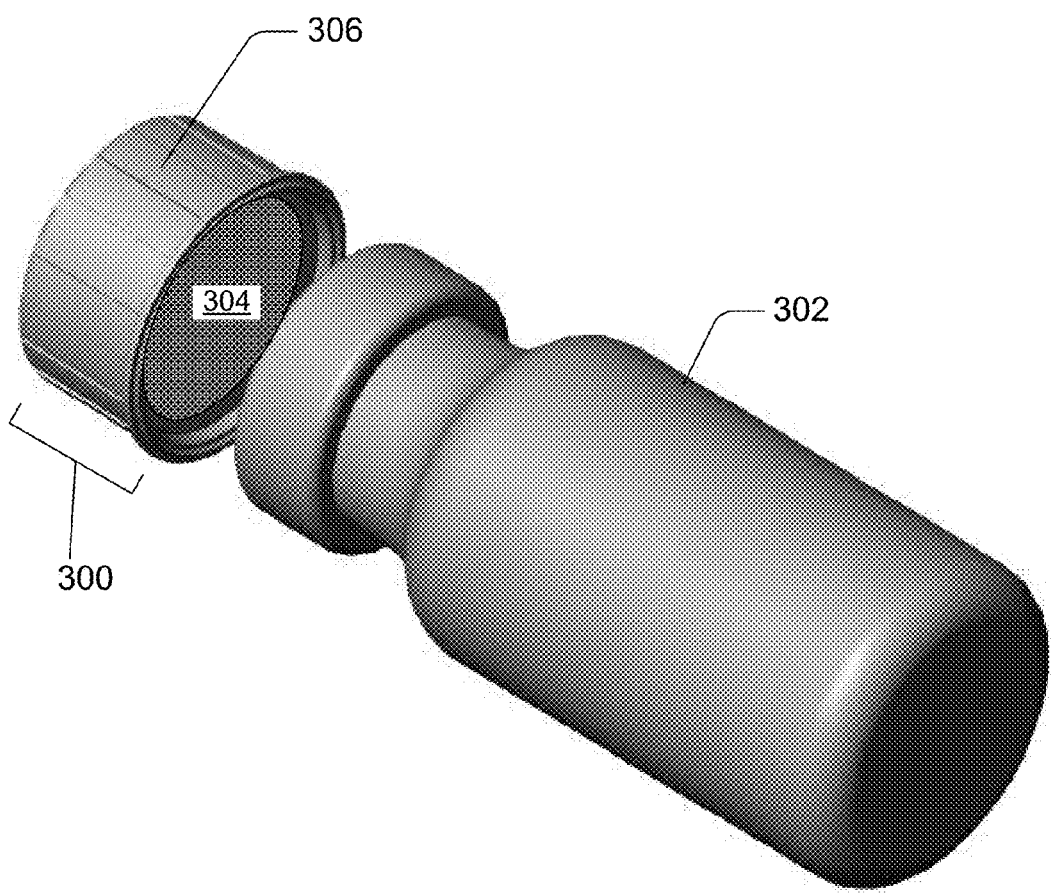
FIG. 3 illustrates an example protective cap device.

FIG. 3 shows an illustration of an example protective cap device 300 that may attach to the neck and exposed elastomeric stopper of a multiple use/dose vial ("vial") 302 after the vial is opened. The example protective cap device 300 having a cylindrical cavity that includes a foam insert 304 carrying an antimicrobial composition, such as the antimicrobial composition described in the preceding section. The example protective cap device 300 may be placed on a vial to protect the vial from microbial and particulate contamination while the vial is not in use. The example protective device may comprise caps such as those described in the preceding section.

In the illustrated example of FIG. 3, the outer surface of the example protective cap device 300 is shown to have a specific texture 306 that may aid the user in gripping the example protective cap device. However, the texture of the example protective cap device is not limited to such texture. Additionally or alternatively, the example protective cap device 300 may be any color that may, for example, aid the user in quick initial identification of the vial. For example, a vial used frequently in an emergency setting (e.g., emergency room, ambulance, etc.) may have a red protective cap. Additionally or alternatively, the size of the example protective cap device 300 can vary based in part on the size of the vial. The example protective cap device 300 is shown as having a round shape, although alternative shapes are contemplated such as, for example, a square shape, a rectangular shape, an oval shape, a polygon shape, and the like. Generally, however, an opening of the protective cap device is shaped and sized to accommodate and protect the vial 302.

In some embodiments, the example protective cap device may include a label area for labeling by the user and/or the placement of an identification tag or tracking barcode.

As shown in FIG. 3, the inner surface within the cavity of the example protective cap device contains a foam insert 304. The foam insert 304, as shown in greater detail in FIG. 4, comprises a foam material having an open-cell region 400 around the circumference of the sides of the cylinder and a closed-cell region 402 on one or both axial ends of the cylinder. Example materials for the composition of the foam insert 304 include, but are not limited to, polyurethane, silicone, silicone rubber, polyethylene, polypropylene, and/or thermoplastic elastomer. The open-cell region 400 of the foam insert has a porous structure that allows an antimicrobial composition, such as the antimicrobial composition described above, to be disposed throughout all or part of the open-cell region 400. The closed-cell region 402 of the foam insert has a non-porous structure that is designed to interface with the metal ring and elastomeric stopper on the vial. The closed-cell region 402 of the foam insert may provide a barrier and prevent a contaminant from entering the elastomeric stopper of the vial and/or prevent contents of the vial from escaping.

Furthermore, the closed-cell region prevents substantial amounts of the antimicrobial composition from entering the vial. In some embodiments, the closed-cell region may have different surface finishes, treatments, or contours (e.g., macro-, micro-, or nano-structures, etc.) to facilitate gripping and/or scrubbing of the vial.

Figure 4:
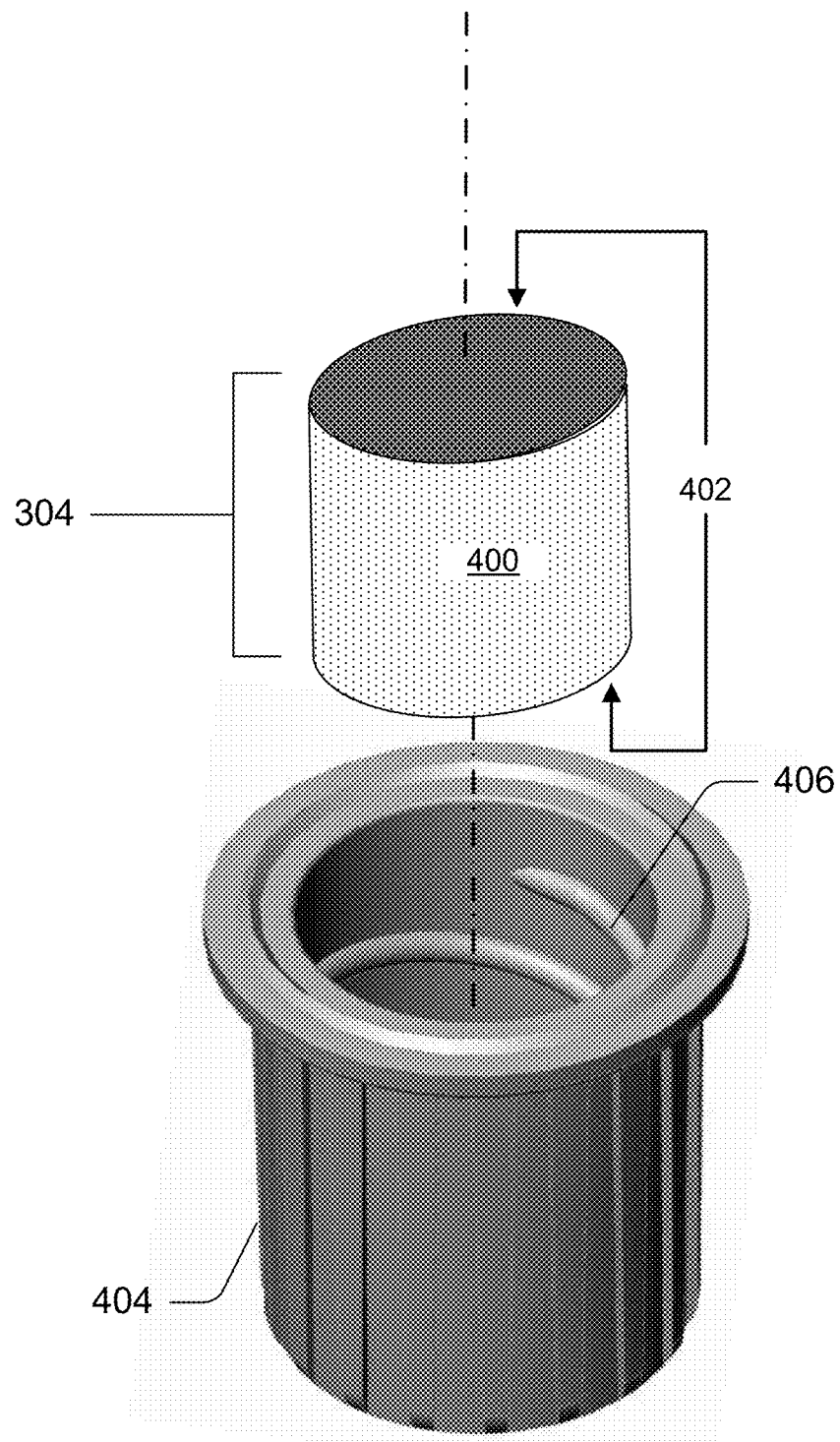
FIG. 4 illustrates an example foam applicator of an example combine cap applicator or an example protective device.
Figure 5A:
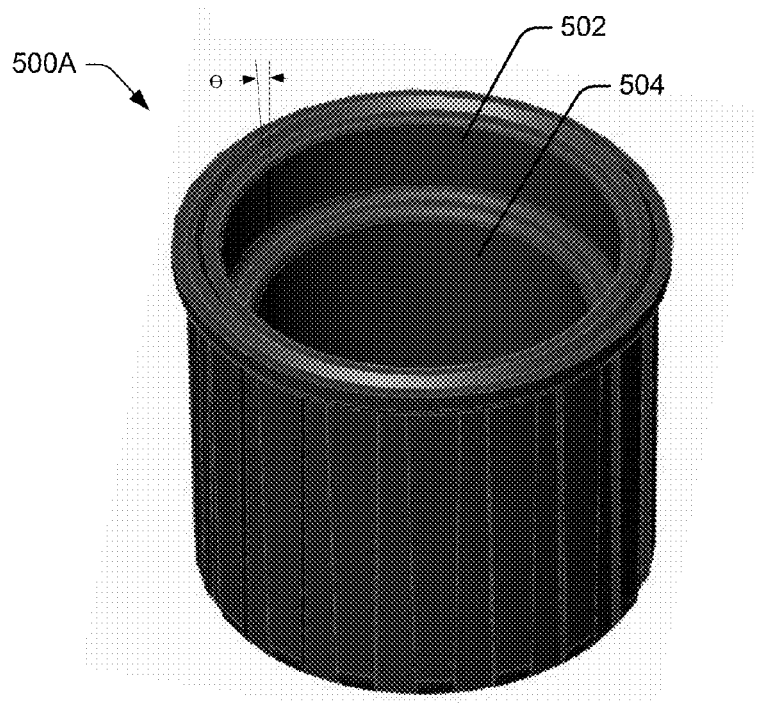
FIGS. 5A-5C illustrate various mechanisms for attachment of an example combine cap applicator or an example protective device.
Figure 5B:
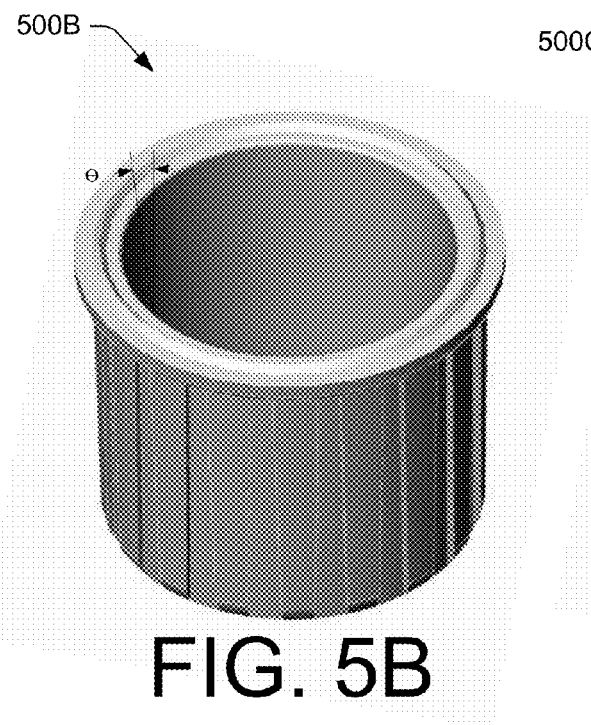
Figure 5C:
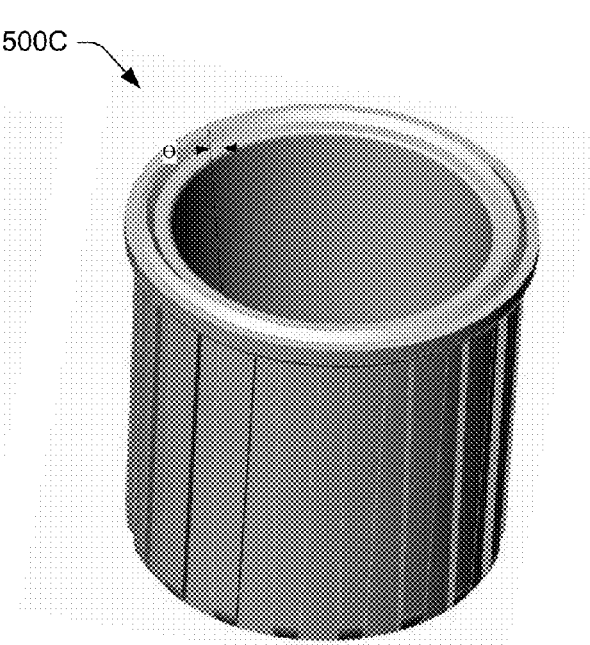

FIGS. 4-5C illustrate several example mechanisms for attaching the example protective cap device to a vial. As shown in FIG. 4, the inner surface of the example protective cap device 404 includes threads 406 molded into the inner surface of the cavity. This attachment feature may allow the user to thread in a twisting motion the example protective cap device onto the vial. In this embodiment, the threads may be used to take advantage of and act upon the anatomical features of the neck of a vial.

FIG. 5A illustrates an example protective cap device 500A having a stepped inner surface, including a first inner surface 502 and a second inner surface 504, the second inner surface 504 having a smaller average diameter than the first inner surface. The first and second inner surfaces 502 and 504 may have diameters chosen to match outer diameter ("OD") of common vials on the market, of maximum and minimum ODs of vials on the market, or based on other criteria. Further both of the first and second inner surfaces 502 and 504 may be tapered (i.e., have a draft angle θ), such that a diameter of the first and second inner surfaces is largest closest to an opening of the example protective cap device 500A and decreases toward the bottom, closed end of the example protective cap device. A draft angle of the first inner surface 502 may be the same as, greater than, or less than a draft angle of the second inner surface 504. When the example protective cap device 500A is placed on a vial, the example protective cap device 500A will slide over the vial until an OD of the vial contacts and seals against the interior surface of the example protective cap device 500A at either the first inner diameter 502 (in the case of a vial with a relatively large OD) or the second inner diameter 504 (in the case of a vial with a relatively small OD).

FIGS. 5B and 5C illustrate alternative embodiments of slip fit protective cap devices 500B and 500C, respectively, which have continuous, smooth inner surfaces. Rather than being stepped as in the embodiment of FIG. 5A, the protective cap devices 500B and 500C have continuous, smooth inner surfaces. The inner surfaces of the protective cap devices 500B and 500C are tapered to accommodate vials of varying OD. However, in order to accommodate vials having a wide range of ODs, the draft angle θ of the protective cap devices needs to be larger (i.e., a more pronounced taper) as in the case of protective cap device 500B, and/or the protective cap device needs to be made deeper, as in the case of protective cap device 500C.

In other embodiments, the example protective cap device may be constructed with a flange on the inner surface at the opening of the cavity. The inner surface of the example protective cap device may otherwise have a continuous smooth surface. In this embodiment, the size of the flange may vary depending, in part, on the OD of the neck of the vial. When the example protective cap device in this embodiment is placed over the vial the flange allows the example protective cap to snap into place over the neck of the vial.

In still other embodiments, the example protective cap device may have internal slits in the cap that run from the opening of the cavity toward the closed end of the example protective cap device. The slits may expand only part way through the wall of the cap such that the cap still provides a seal to prevent contamination of the vial. The internal slits in the example protective cap device would allow for the cap to expand enveloping a portion of the vial as the example protective cap device is slid over the vial.

In still other embodiments, the example protective cap device may have a wire mechanism located within or around the cavity to allow for attachment to a vial. The wire mechanism may take the form of a spring. As with the example threads 406 in FIG. 4, the wire mechanism may allow a user to twist, squeeze, crimp, or otherwise fix the example protective cap device securely to the vial. Any of the above-listed attachment embodiments may be used separately or in conjunction with another to attach the example protective cap device to the vial.

Example Packaging of Protective Cap Device

Any of the example protective cap devices described above may be sterilely packaged individually or in kits of multiple devices in a variety of packages. Furthermore, the protective cap devices themselves may additionally or alternatively be housed in a packaging that contains UV protective materials to inhibit breakdown of the antimicrobial composition.

FIGS. 6A-6C illustrate three example ways of packaging the example protective cap devices described herein. As shown in FIG. 6A, each protective cap device may be individually sealed in a pouch or packet 600 by sandwiching the protective cap device between multiple layers of thermoplastic material and sealing the sheets of material to each other around a periphery of the protective cap device by, for example, sonic welding, microwave welding, thermal bonding, or the like.

The approach described in FIG. 6A may be extended to simultaneously package multiple protective cap devices in a strip by placing multiple protective cap devices between sheets of thermoplastic material and then sealing the sheets of material to each other around the peripheries of each of the protective cap device using any of the sealing methods described above. The result is a strip 602, as illustrated in 6B, containing multiple individually sealed protective cap devices. Individual protective cap devices may then by dispensed by cutting between the protective cap devices in the strip 602. Alternatively, the strip 602 may include perforations or score lines between the individual protective cap devices in the strip 602.

In another embodiment, as shown in FIG. 6C, a package may include multiple protective cap devices that have the opened end of the cavity bonded directly in a tape or strip 604. The tape or strip 604 may be packaged according to the methods described with reference to FIGS. 6A and/or 6B, or other methods. In some embodiments, the multiple protective cap devices on tape or strip 604 may be of different sizes, different antimicrobial compositions and/or different concentrations of antimicrobial compositions.

Other Cap Devices

In some examples, cap devices such as those described herein as well as in U.S. Pat. No. 7,763,006 to Tennican, U.S. Pat. No. 7,799,010 to Tennican, and U.S. Pat. No. 7,792,322 to Tennican, and/or U.S. Provisional Patent Application No. 61/564,206, filed Nov. 28, 2011 to Tennican et al., all of which are incorporated herein by reference, may be used with syringe devices, such as mixing administration syringes described in U.S. Pat. No. 7,635,344 to Tennican et al., U.S. Pat. No. 7,731,678 to Tennican et al., U.S. Pat. No. 7,731,679 to Tennican et al., U.S. Pat. No. 7,749,189 to Tennican et al., U.S. Pat. No. 7,753,891 to Tennican et al., U.S. Pat. No. 7,776,011 to Tennican et al., U.S. Pat. No. 7,985,211 to Tennican et al., U.S. Pat. No. 8,002,737 to Tennican, U.S. Pat. App. Pub. No. 2007/0167910 filed Nov. 9, 2006 to Tennican et al., U.S. Pat. App. Pub. No. 2007/0249996 filed May 21, 2007 to Tennican et al., and U.S. Pat. App. Pub. No. 2011/0272310 filed Jul. 15, 2011 to Tennican, which are also incorporated herein by reference.

For example, the cap devices may be packaged with a syringe (e.g., a mixing administration syringe) in accordance with the methods described in the preceding sections, or in other methods. The cap devices may be packaged in a sterile packaging along with a syringe in the same compartment of the sterile packaging or in a separate compartment of the sterile packaging. Alternatively, one or more cap devices may be packaged separately from the syringe.

In some examples, one or more cap devices may be coupled in, on, or to the plunger, wings, tip, or other portion of the syringe. In that case, the cap devices may be sealed directly to the syringe body, or may be sealed by a separate removable film or cover.

The cap device may be placed on the port access line or IV device after the mixing administrative syringe has been used on the port access line or IV device and/or an injection or blood draw site.

In some embodiments, a cap device may be used to clean, sanitize and/or disinfect on a surface (e.g., skin or tissue) prior to using the mixing administrative syringe. For example, the cap device may be used to clean an injection site prior to using the mixing administrative syringe at the injection site.

In some embodiments, a cap device may be placed on the mixing administrative syringe to disinfect the syringe prior to use. Additionally or alternatively, a cap device may be placed on a vial of medication or diluents to disinfect the vial prior to use, between uses, and/or during storage.

CONCLUSION

Although the disclosure describes embodiments having specific structural features and/or methodological acts, it is to be understood that the claims are not necessarily limited to the specific features or acts described. Rather, the specific features and acts are merely illustrative some embodiments that fall within the scope of the claims of the disclosure.

What is claimed is:

1. A medical device comprising:
a first cap detachably coupled to a second cap, wherein each cap comprises:
 a cavity;
 an outer surface configured to interface with a user;
 an inner surface within the cavity; and
 a foam applicator material attached to the inner surface within the cavity containing a cleansing, antiseptic or antimicrobial agent comprising:
  from about 5 mg/mL to about 50 mg/mL of ethylenediaminetetraacetic acid (EDTA), acids of EDTA, salts of EDTA, citrate, salts of citrate or any combination thereof;
  from about 20% to about 70% ethanol, by volume;
  from about 0.5% to about 7.5% hydrogen peroxide, by volume; and
  water.

2. The medical device as recited in claim 1, wherein the foam applicator material comprises a shape substantially similar to a shape of each cavity of each cap.

3. The medical device as recited in claim 1, wherein the foam applicator material of at least one cap is maintained in a compressed state while the first and second caps are coupled and the foam applicator material of at least one cap is configured to extend outside the cavity when the first cap is detached from the second cap.

4. The medical device as recited in claim 1, wherein the foam applicator material comprises a permeable material with different surface treatments, finishes, contours, or combinations thereof.

5. The medical device as recited in claim 1, wherein the first and second cap comprise starch polymer, cellulosic gel, polyurethane, silicone, silicone rubber, polyethylene, polypropylene, thermoplastic elastomer or mixtures thereof.

6. The medical device as recited in claim 1, wherein the first and second cap comprise polypropylene, polyethylene, copolymer material or mixtures thereof.

7. The medical device as recited in claim 1, wherein the first and second cap are coupled by at least one of a thread, a snap fit flange, a snap fit channel, a molded feature or combination thereof.

8. The medical device as recited in claim 1, wherein the foam applicator material of the first cap comprises a cleansing, antiseptic or antimicrobial agent different from a cleansing, antiseptic or antimicrobial in the second cap.

9. A method comprising:
obtaining a device comprising a first cap detachably coupled to a second cap, wherein the first cap and the second cap each comprise an interior cavity for storing an applicator and the applicator of at least one of the first cap and second cap comprises a cleansing, antiseptic or antimicrobial agent comprising:
 from about 5 mg/mL to about 50 mg/ml of ethylenediaminetetraacetic acid (EDTA), acids of EDTA, salts of EDTA, citrate, salts of citrate or any combination thereof;
 from about 20% to about 70% ethanol, by volume;
 from about 0.5% to about 7.5% hydrogen peroxide, by volume; and
 water;
detaching the first cap from the second cap;
applying the applicator of the first cap to a surface; and
securing the second cap to the surface.

10. The method as recited in claim 9, wherein the applicator of the first cap is configured to extend outside the interior cavity when the first cap is detached from the second cap.

11. The method as recited in claim 9, wherein the surface is at least one of an intravascular line valve, intravascular line port, or an intravascular line injection site.

12. The method as recited in claim 9, wherein detaching the first cap from the second cap further comprises at least one of twisting, pulling, snapping or bending the first cap away from the second cap.

13. The method as recited in claim 9, wherein the applicator of the second cap further comprises an open-cell inner layer configured to store the cleansing, antiseptic or antimicrobial agent, the open-cell inner layer connecting two closed-cell outer layers at a top and a bottom of the applicator.

14. The method as recited in claim 9, wherein the antiseptic or antimicrobial agent is a gel.

15. A medical device for protecting a multiple use vial from contamination comprising:
a cap having a cylindrical cavity, the cap having an outer surface configured to interface with a user and an inner surface within the cylindrical cavity to interface with the vial;
a foam insert contained within the cylindrical cavity of the cap, the foam insert having an inner open-cell porous layer between two outer closed-cell non-porous layers; and
an infection inhibiting solution disposed within the inner open-cell porous layer, the infection inhibiting solution comprises:

from about 5 mg/mL to about 50 mg/ml of ethylenediaminetetraacetic acid (EDTA), acids of EDTA, salts of EDTA, citrate, salts of citrate or any combination thereof;

from about 20% to about 70% ethanol, by volume;

from about 0.5% to about 7.5% hydrogen peroxide, by volume; and water.

16. The medical device of claim 15, wherein the inner surface of the cylindrical cavity of the cap comprises one of a tapered stepped surface, a stepped surface, a snap fit flange, threads or internal slits to allow for attachment of the cap to the multiple use vial.

17. The medical device of claim 15, wherein the outer surface of the cap includes a labeling or barcode placement area.

18. The medical device of claim 15, wherein at least one of the outer closed-cell non-porous layers of the foam has a surface treatment, finish, contour, or combination thereof.

19. The medical device of claim 15, wherein the infection inhibiting solution disposed within the inner open-cell porous layer provides a visual indication of contamination when an infectious agent is present on a surface of the multiple use vial.

* * * * *